(12) United States Patent
de Haas

(10) Patent No.: US 10,383,957 B2
(45) Date of Patent: Aug. 20, 2019

(54) NEAR-INFRARED FLUORESCENT SURGICAL DYE MARKERS

(71) Applicant: Anthony H. de Haas, Pawleys Island, SC (US)

(72) Inventor: Anthony H. de Haas, Pawleys Island, SC (US)

(73) Assignee: Anthony H. de Haas, Pawleys Island, SC (US)

( * ) Notice: Subject to any disclaimer, the term of this patent is extended or adjusted under 35 U.S.C. 154(b) by 774 days.

(21) Appl. No.: 14/986,808

(22) Filed: Jan. 4, 2016

(65) Prior Publication Data

US 2016/0193365 A1    Jul. 7, 2016

Related U.S. Application Data

(60) Provisional application No. 62/100,298, filed on Jan. 6, 2015, provisional application No. 62/215,783, filed on Sep. 9, 2015.

(51) Int. Cl.
| | | |
|---|---|---|
| *A61K 9/00* | (2006.01) | |
| *A61K 49/00* | (2006.01) | |
| *A61B 5/00* | (2006.01) | |
| *A61B 90/00* | (2016.01) | |

(52) U.S. Cl.
CPC ........ *A61K 49/0091* (2013.01); *A61B 5/0071* (2013.01); *A61K 49/003* (2013.01); *A61K 49/0034* (2013.01); *A61B 2090/3941* (2016.02)

(58) Field of Classification Search
CPC ................................................ A61K 49/0091
See application file for complete search history.

(56) References Cited

U.S. PATENT DOCUMENTS

| 3,015,128 A | 1/1962 | Somerville, Jr. |
| 3,293,114 A | 12/1966 | Kenaga et al. |
| 3,401,475 A | 9/1968 | Morehouse et al. |
| 3,479,811 A | 11/1969 | Walters |
| 3,488,714 A | 1/1970 | Walters et al. |
| 3,594,326 A | 7/1971 | Himmel |
| 3,732,172 A | 5/1973 | Herbig et al. |
| 3,915,972 A | 10/1975 | Altermatt |

(Continued)

FOREIGN PATENT DOCUMENTS

| EP | 1 736 778 A1 | 12/2006 |
| EP | 2 545 906 A1 | 1/2013 |
| WO | WO 97/39064 | 10/1997 |
| WO | WO 02/07587 | 1/2002 |
| WO | WO 2011/053803 A2 | 5/2011 |

OTHER PUBLICATIONS

International Search Report and Written Opinion for PCT/US2016/012020 dated Apr. 1, 2016, 9 pages.

(Continued)

*Primary Examiner* — Paul W Dickinson
(74) *Attorney, Agent, or Firm* — Dority & Manning, P.A.

(57) ABSTRACT

The potential use of a PMMA encapsulated near-infrared fluorescent dye includes endoscopic tattooing of intestinal neoplasms, location visualization of non-palpable breast lesions, and, but not limited to, location/visualization of soft tissue lesions in difficult anatomic regions. Commercially available fluorescent imaging systems, both open and laparoscopic, would be used in conjunction to fluoresce these marked tissues, augmenting the surgeon's ability to intraoperatively locate the correct lesion to resect.

24 Claims, 4 Drawing Sheets

(56) References Cited

U.S. PATENT DOCUMENTS

| | | | |
|---|---|---|---|
| 3,945,956 A | 3/1976 | Garner | |
| 4,108,806 A | 8/1978 | Cohrs et al. | |
| 4,179,546 A | 12/1979 | Garner et al. | |
| 4,420,442 A | 12/1983 | Sands | |
| 4,421,562 A | 12/1983 | Sands | |
| 4,540,629 A | 9/1985 | Sands et al. | |
| 4,549,892 A | 10/1985 | Baker et al. | |
| 4,603,209 A | 7/1986 | Tsien et al. | |
| 4,774,339 A | 9/1988 | Haugland et al. | |
| 4,810,636 A | 3/1989 | Corey | |
| 4,812,409 A | 3/1989 | Babb et al. | |
| 4,822,534 A | 4/1989 | Lencki et al. | |
| 4,849,362 A | 7/1989 | DeMarinis et al. | |
| 4,898,734 A | 2/1990 | Mathiowitz et al. | |
| 4,945,171 A | 7/1990 | Haugland et al. | |
| 5,187,288 A | 2/1993 | Kang et al. | |
| 5,227,487 A | 7/1993 | Haugland et al. | |
| 5,242,805 A | 9/1993 | Naleway et al. | |
| 5,248,782 A | 9/1993 | Haugland et al. | |
| 5,268,486 A | 12/1993 | Waggoner et al. | |
| 5,274,113 A | 12/1993 | Kang et al. | |
| 5,433,896 A | 7/1995 | Kang et al. | |
| 5,442,045 A | 8/1995 | Haugland et al. | |
| 5,451,343 A | 9/1995 | Neckers et al. | |
| 5,459,276 A | 10/1995 | Kuhn et al. | |
| 5,486,616 A | 1/1996 | Waggoner et al. | |
| 5,501,980 A | 3/1996 | Katerinopoulos et al. | |
| 5,569,587 A | 10/1996 | Waggoner | |
| 5,569,766 A | 10/1996 | Waggoner et al. | |
| 5,627,027 A | 5/1997 | Waggoner | |
| 5,696,157 A | 12/1997 | Wang et al. | |
| 5,798,276 A | 8/1998 | Haugland et al. | |
| 5,830,912 A | 11/1998 | Gee et al. | |
| 5,846,737 A | 12/1998 | Kang | |
| 5,847,162 A | 12/1998 | Lee et al. | |
| 6,017,712 A | 1/2000 | Lee et al. | |
| 6,025,505 A | 2/2000 | Lee et al. | |
| 6,048,982 A | 4/2000 | Waggoner | |
| 6,080,852 A | 6/2000 | Lee et al. | |
| 6,130,101 A | 10/2000 | Mao et al. | |
| 6,162,931 A | 12/2000 | Gee et al. | |
| 6,229,055 B1 | 5/2001 | Klaubert et al. | |
| 6,339,392 B1 | 1/2002 | Ashihara | |
| 6,348,599 B1 | 2/2002 | Cummins et al. | |
| 6,403,807 B1 | 6/2002 | Singh et al. | |
| 6,562,632 B1 | 5/2003 | Szalecki et al. | |
| 6,664,047 B1 | 12/2003 | Haugland et al. | |
| 6,716,979 B2 | 4/2004 | Diwu et al. | |
| 9,143,746 B2 | 9/2015 | Westwick et al. | |
| 2002/0044909 A1 | 4/2002 | Achilefu et al. | |
| 2005/0106711 A1 | 5/2005 | Chari et al. | |
| 2008/0138289 A1 | 6/2008 | Goronkin et al. | |
| 2008/0154102 A1 | 6/2008 | Frangioni et al. | |
| 2010/0196280 A1 | 8/2010 | Fischer et al. | |
| 2010/0286529 A1 | 11/2010 | Carroll et al. | |
| 2012/0114563 A1 | 5/2012 | Carter et al. | |
| 2012/0276015 A1 | 11/2012 | Mauro et al. | |
| 2013/0030282 A1 | 1/2013 | Margel et al. | |
| 2013/0209368 A1 | 8/2013 | Magdassi et al. | |
| 2013/0331690 A1 | 12/2013 | Healey et al. | |
| 2013/0336889 A1 | 12/2013 | Shieh et al. | |
| 2015/0343084 A1* | 12/2015 | Dilley | A61K 41/0071 604/20 |

OTHER PUBLICATIONS

Abstract of Article, Ashida et al., Indocyanine green is an ideal dye for endoscopic ultrasound-guided fine-needle tattooing of pancreatic tumors, Endoscopy, vol. 38, No. 2, Feb. 2006, 1 page.
Abstract of Article, Bedocs et al., Invisible tattoo granuloma, Cutis, vol. 81, No. 3, Mar. 2008, 1 page.
Abstract of Article, Hammond et al., Endoscopic tattooing of the colon: clinical experience, vol. 59, No. 3, Mar. 1993, 1 page.
Abstract of Article, HG Moore, Colorectal cancer: what should patients and families be told to lower the risk of colorectal cancer?, Surgical Oncology Clinics of North America, vol. 19, No. 4, 1 page.
Abstract of Article, Jeffrey L. Ponsky et al., Endoscopic marking of colonic lesions, Gastrointestinal Endoscopy, vol. 22, No. 1, Aug. 1975, 1 page.
Abstract of Article, Endoscopic lovalizaiton of colon cancers, Vignati, et al., Surgical Endoscopy, vol. 8, No. 9, Sep. 1994, 1 page.
Walter J. Akers et al., Predicting in vivo fluorescence lifetime behavior of near-infrared fluorescent contrast agents using in vitro measurements, Journal of Biomedical Optics, vol. 13, No. 5, Sep./Oct. 2008, 9 pages.
Matthew P. Askin, MD, et al., Tattoo of colonic neoplasms in 113 patients with a new sterile carbon compount, Gastrointestinal Endoscopy, vol. 56, No. 3, Jan. 11, 2002, 4 pages.
Britton Chance, Near-Infrared Images Using Continuous, Phase-Modulated, and Pulsed Light with Quantitation of Blood and Blood Oxygenation, Article, Feb. 7, 2006, 18 pages.
Yong Beom Cho et al., Tumor Localization for Laparoscopic Colorectal Surgery, World Journal of Surgery, vol. 31, May 30, 2007, 6 pages.
Gary S. Chuang, MD, et al., Ultraviolet-Fluorescent Tattoo Location of Cutaneous Biopsy Site, American Society for Dermatologic Surgery, Inc., vol. 38, No. 3, Mar. 2012, 5 pages.
Alex M. De Grand, An Operational Near-Infrared Fluorescence Imaging System Prototype for Large Animal Surgery, Technology in Cancer Research & Treatment, vol. 2, No. 6, Dec. 2003, 10 pages.
Christos Feretis, MD, et al., Endoscopic implantation of Plexiglas (PMMA) microspheres for the treatment of GERD, American Society for Gastrointestinal Endoscopy, vol. 53, No. 4, Jan. 3, 2001, 4 pages.
John V. Frangioni, In vivo near-infrared fluorescence imaging, Current Opinion in Chemical Biology, vol. 7, 2003, 9 pages.
Sylvain Gioux et al., Image-Guided Surgery using Invisible Near-Infrared Light: Fundamentals of Clinical Translation, NIH Public Access Author Manuscript, vol. 9, No. 5, Oct. 2010, 31 pages.
Jan P. Kamler, MD et al., Endoscopic lower esophageal sphincter bulking for the treatment of GERD: safety evaluation of injectable polymethylmethacrylate microspheres in miniature swine, American Society for Gastrointestinal Endoscopy, vol. 72, No. 2, Feb. 14, 2010, 6 pages.
Sripathi R. Kethu, MD, et al., Endoscopic tattoing, Technology Status Evaluation Report, vol. 72, No. 4, 2010, 5 pages.
Tashiyuki Kitai et al., Fluorescence Navigation with Indocyanine Green for Detecting Sentinel Lymph Nodes in Breast Cancer, Breast Cancer Article, vol. 12, No. 3, Jul. 2005, 5 pages.
Gottfried Lemperle et al., Urethral Bulking with Polymethylmethacrylate Microspheres for Stress Urinary Incontinence: Tissue Persistence and Safety Studies in Miniswine, Basic and Translational Science Study, vol. 77, No. 4, Dec. 13, 2010, 7 pages.
Nasrin Mani, MD, et al., Novel use of polymethyl methacrylate (PMMA) microspheres in the treatment of infraorbital rhytids, Journal of Cosmetic Dermatology, vol. 12, Sep. 5, 2013, 7 pages.
Norikatsu Miyoshi et al., Surgical usefulness of indocyanine green as an alternative to India ink for endoscopic marking, Surgical Endoscopy, vol. 23, Apr. 28, 2008, 6 pages.
Akira Nakayama, MD et al., Functional Near-Infrared Fluorescence Imaging for Cardiac Surgery and Targeted Gene Therapy, Molecular Imaging, vol. 1, No. 4, Oct. 2002, 13 pages.
Vasilis Ntziachristos et al., Fluorescence imaging with near-infrared light: new technological advances that enable in vivo molecular imaging, Center for Molecular Imaging Research, vol. 13, Jul. 19, 2002, 15 pages.
Nicole Piscatelli, MD, et al., Localizing Colorectal Cancer by Colonoscopy, Arch Surg., vol. 140, Oct. 2005, 4 pages.
J.P. Sauntry, MD, et al., A Technique for Making the Mucosa of the Gastrointestinal Tract After Polypectomy, Jul. 30, 1957, 4 pages.
Eva M Sevick-Muraca et al., Fluorescence-enhances, near infrared diagnostic imaging with contrast agents, Current Opinion in Chemical Biology, vol. 5, 2002, 9 pages.
David P. Taggart, MD., et al., Preliminary Experience with a Novel Intraoperative Fluorescence Imaging Technique to Evaluate the

(56) References Cited

OTHER PUBLICATIONS

Patency of Bypass Grafts in Total Arterial Revascularization, The Society of Thoracic Surgeons, vol. 75, 2003, 4 pages.

Eiichi Tanaka, MD., PHD et al., Image-Guided Oncologic Surgery Using Invisible Light: Completed Pre-Clinical Development for Sentinel Lymph Node Mapping, NIH Public Access Author Manuscript, vol. 13, No. 12, Dec. 2006, 17 pages.

George Themelis et al., Real-time intraoperative Fluorescence imaging system using light-absorption correction, Journal of Biomedical Optics, vol. 14, No. 6, Nov./Dec. 2009, 9 pages.

Susan L. Troyan, MD. et al., The FLARE™ Intraoperative Near-Infrared Fluorescence Imaging System: A First-in-Human Clinical Trial in Breast Cancer Sentinel Lymph Node Mapping, NIH Public Access Author Manuscript, vol. 16, No. 10, Oct. 2009. 17 pages.

Makoto Watanabe et al., Colonic Tattooing Using Fluorescence Imaging with Light-Emitting Diode-Activated Indocyanine Green: A Feasibility Study, Surgery Today, vol. 39, 2009, 5 pages.

Lin et al., "Fabrication of biodegradable polyurethane microspheres by a facile and green process", Society for Biomaterials, Aug. 28, 2014, 10 pages.

Jorge O. Escobedo et al., NIR Dyes for Bioimaging Applications, Curr Opin Chem Biol. vol. 14, No. 1, 11 pages, Feb. 2010.

Summer L. Gibbs, Near infrared fluorescence for image-guided surgery, Quant Imaging Med Surg, vol. 2, No. 3, 11 pages, Sep. 2012, pp. 177-187.

John V. Frangioni et al., Image-Guided Surgery using Invisible Near-Infrared Light: Fundamentals of Clinical Translation, Mol Imaging, vol. 9, No. 5, 23 pages, Oct. 2010, pp. 237-255.

\* cited by examiner

NEAR-INFRARED FLUORESCENT SURGICAL DYE MARKERS

RELATED APPLICATIONS

The present application claims priority to U.S. Provisional Application Ser. No. 62/100,298, filed on Jan. 6, 2015, and U.S. Provisional Application Ser. No. 62/215,783, filed on Sep. 9, 2015, which are incorporated herein in their entirety by reference thereto.

BACKGROUND OF THE INVENTION

In the workup of a non-palpable, radiographic, and/or difficult to locate anatomic tissue (e.g., a lesion such as a tumor, wound, ulcer, abscess, etc. or even healthy tissue) in surgery, the location of this tissue is typically inked, tattooed, or physically oriented with needle/wires to direct the surgeon for excision or to monitor the tissue over time. Examples of lesions include, but are not limited to, neoplasms in the intestine, radiographic breast lesions, neurologic lesions, or soft tissue masses elsewhere in the body. Again, these lesions are either non-palpable, in a tissue location that is difficult to visualize, and/or have characteristics, such as lymph node drainage, that can make visualizing the tissue during surgery extremely difficult. Additionally, lymph nodes are often difficult to locate, visualize, and map.

Currently, carbon-based ink or radioactive agents are used by surgeons to mark tissue that is often difficult to visualize during surgery or to map lymph nodes during, for example, sentinel lymph node mapping. Nevertheless, carbon-based ink is often difficult to see, and radioactive agents put the patient at risk for radiation exposure. Moreover, while fluorescent inks or dyes have been utilized, the lack of stability and tendency of fluorescent inks to migrate to other areas outside the tissue or lymph nodes of interest have made their use problematic. For instance, surgeons may inject nano-sized fluorescent dye particles intravascularly with the hope that the particles will eventually reach the tissue of interest, such as cancerous tissue, due to the permeability changes of cells affected by cancer, thus allowing the particles to enter the tissue. However, such small particles often degrade with time and can also migrate out of the area of interest. Furthermore, such small particles often require a coating with a surfactant or protein in an attempt to limit the degradation of the particles and/or concentrate or direct the particles to the tissue of interest. As such, a need exists for effective tattooing for the visualization of non-palpable tissue and/or lymph nodes that does not degrade, that does not migrate, and that can be directly injected into the tissue of interest. In other words, a need exists for a fluorescent ink or dye for marking tissue (e.g., healthy tissue or lesions) or lymph nodes of interest that is stable, exhibits minimal degradation, and does not migrate once it is introduced to the tissue or lymph node of interest.

SUMMARY OF THE INVENTION

In accordance with one embodiment of the present invention, a method for marking and visualizing tissue is provided. The method includes directly injecting a carrier fluid containing a near-infrared fluorescent dye encapsulated by polymeric microspheres into the tissue to mark the tissue, wherein the polymeric microspheres have a particle size of from about 40 micrometers to about 150 micrometers; applying a light source to an area near the tissue, wherein the light source is applied at a wavelength sufficient to excite the near-infrared fluorescent dye; and observing the marked tissue on a display.

In some embodiments, the tissue can be a lesion or healthy tissue. For example, the lesion can be a tumor. Further, the tissue can be intestinal tissue, breast tissue, or brain tissue.

In another embodiment, the near-infrared fluorescent dye can have an excitation wavelength of from about 650 nanometers to about 950 nanometers.

In still another embodiment, the near-infrared fluorescent dye can include methylene blue, indocyanine green, or a combination thereof.

In yet another embodiment, the polymeric microspheres can include polymethylmethacrylate (PMMA), polystyrene, polyacrylonitrile, polyacrylamide, polyvinyl chloride, or a combination thereof. Further, the polymeric microspheres can have a density of from about 1 gram/cubic centimeter to about 1.5 grams per cubic centimeter. Additionally, the polymeric microspheres can be free of a surfactant or protein coating.

In an additional embodiment, the near-infrared fluorescent dye can be present in the carrier fluid in an amount ranging from about 0.01 wt. % to about 10 wt. % based on the wt. % of polymeric microspheres present.

In one particular embodiment, the near-infrared fluorescent dye and polymeric microspheres can be contained within the tissue into which the carrier fluid is directly injected and do not migrate from the tissue.

In one more embodiment, the near-infrared dye encapsulated by the polymeric microspheres can be observed upon application of the light source for a time period of up to about 24 months post-injection.

In another embodiment, the light source and display can be components of a fluorescent imaging system. Further, the marked tissue can be dissected via a laparoscopic surgical procedure or an open surgical procedure.

In accordance with another embodiment of the present invention, an imaging composition for marking a tissue for visualization is provided. The composition includes a near-infrared fluorescent dye encapsulated by polymeric microspheres, wherein the polymeric microspheres have a particle size of from about 40 micrometers to about 150 micrometers.

In one particular embodiment, the composition can be contained in a carrier fluid. Further, the near-infrared fluorescent dye can present in the carrier fluid in an amount ranging from about 0.01 wt. % to about 10 wt. % based on the wt. % of polymeric microspheres present.

In an additional embodiment, the near-infrared fluorescent dye and polymeric microspheres can be contained within the tissue after direct injection into the tissue via the carrier fluid and do not migrate from the tissue.

In still another embodiment, the near-infrared fluorescent dye component of the imaging composition can have an excitation wavelength of from about 650 nanometers to about 950 nanometers.

In yet another embodiment, the near-infrared fluorescent dye component of the imaging composition can include methylene blue, indocyanine green, or a combination thereof. Meanwhile, the polymeric microsphere component of the imaging composition can include polymethylmethacrylate (PMMA), polystyrene, polyacrylonitrile, polyacrylamide, polyvinyl chloride, or a combination thereof.

In one particular embodiment, the polymeric microspheres in the composition can have a density of from about 1 gram per cubic centimeter to about 1.5 grams per cubic centimeter.

In another embodiment, the polymeric microspheres in the composition can be free of a surfactant or protein coating.

In accordance with one more embodiment of the present invention, a system for tissue visualization is provided. The system includes a fluorescent imaging system comprising a light source and a display; and a carrier fluid containing a near-infrared fluorescent dye encapsulated by polymeric microspheres into the tissue to mark the tissue, wherein the polymeric microspheres have a particle size of from about 40 micrometers to about 150 micrometers; wherein applying the light source to an area near the tissue at a wavelength sufficient to excite the near-infrared fluorescent dye facilitates the observation of the marked tissue on the display.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes references to the appended figures in which.

Figure 1:
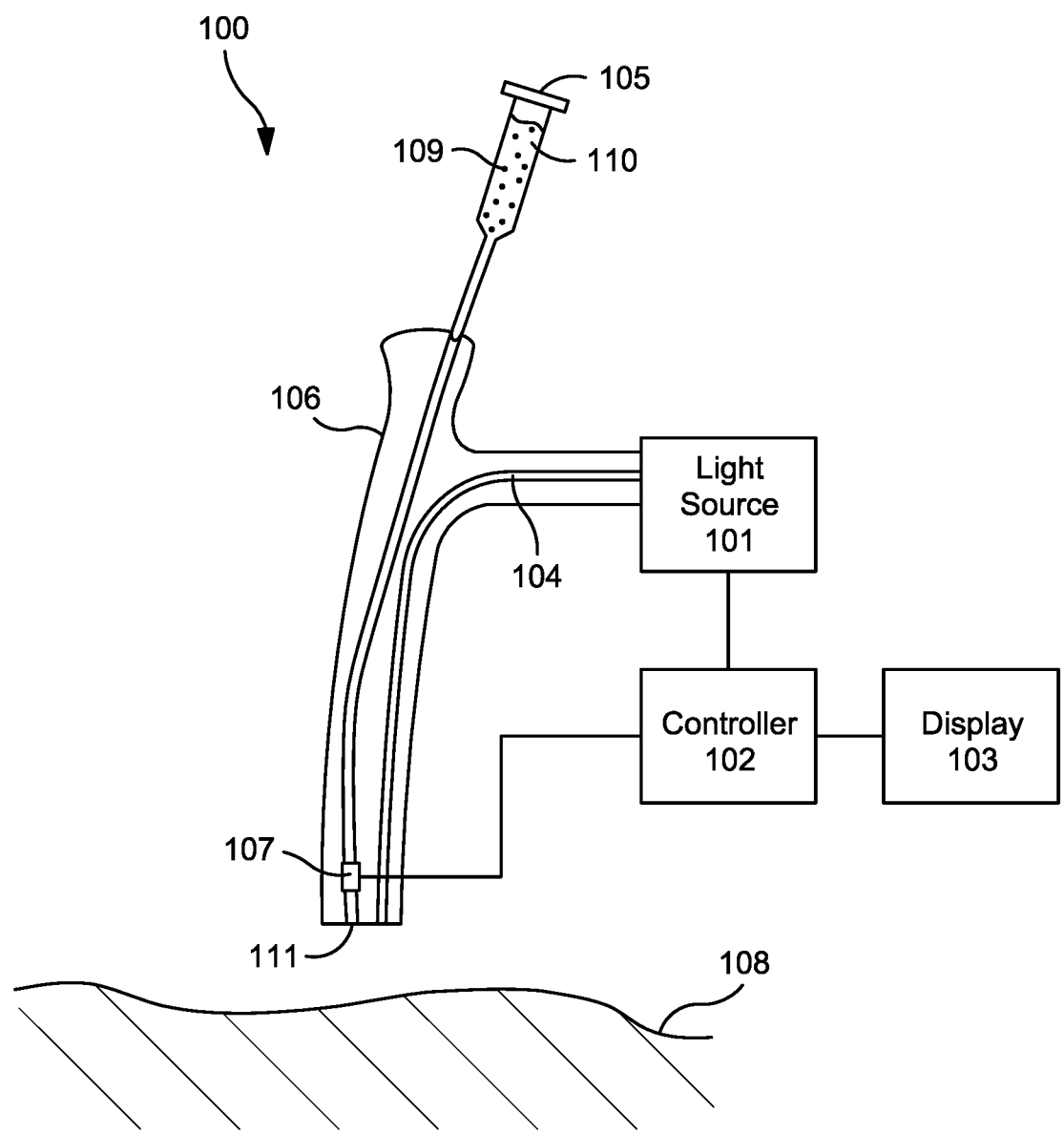
FIG. 1 illustrates a system for marking tissue for visualization according to one embodiment of the present invention.

Repeat use of reference characters in the present specification and drawings is intended to represent same or analogous features or elements of the invention.

DETAILED DESCRIPTION

Reference will now be made in detail to various embodiments of the invention, one or more examples of which are set forth below. Each example is provided by way of explanation of the invention, not limitation of the invention. In fact, it will be apparent to one of ordinary skill in the art that various modifications and variations may be made in the present invention without departing from the scope or spirit of the invention. For instance, features illustrated or described as part of one embodiment may be used on another embodiment to yield a still further embodiment. Thus, it is intended that the present invention covers such modifications and variations as come within the scope of the appended claims and their equivalents.

Generally speaking, the present invention is directed to an imaging composition for marking a tissue for visualization, the imaging composition comprising a near-infrared fluorescent dye encapsulated by polymeric microspheres, wherein the polymeric microspheres have a particle size of from about 40 micrometers to about 150 micrometers, as well as to a method and system for directly injecting the microspheres into the area of interest (e.g., tissue or lymph nodes) for visualization of the area of interest. By selectively controlling the particle size of the microspheres, the present inventor has found that once directly injected into the tissue of interest, the microspheres do not migrate and can be visualized for extended periods of time, such as up to 24 months, even without the use of a surfactant or protein coating as required for existing microspheres that are delivered intravascularly. The various components of the imaging composition are discussed in more detail below, as a well as a system and method for visualization of a tissue of interest via the imaging composition.

Polymeric Microspheres

The present invention contemplates the use of polymeric microspheres to encapsulate a near-infrared fluorescent dye in order to provide real time image guidance to surgeons for visualization of tissue that needs to be resected (e.g., tumors), as well as tissue that needs to be avoided (i.e., blood vessels, nerves, etc.) and organs that need to be monitored (e.g., lymph nodes). The term "polymeric microsphere" as used herein refers to particles of a size typically measured in the range from about 40 micrometers to about 150 micrometers, which can be synthesized by means of chemically-catalyzed addition of monomeric molecules to chemical chains and controlled in such a way as to achieve particles of uniform size distribution and surface composition.

The utility of an in vivo contrast agent (e.g., the imaging composition of the present invention that includes a near-infrared fluorescent dye or fluorophore encapsulated by polymeric microspheres) depends on preferential accumulation of the contrast agent or imaging composition in target tissue and achievement of sufficient signal-to-noise ratios to yield satisfactory image resolution. After injection into a subject directly into the tissue or lymph node of interest, the polymeric microspheres accumulate in the tissue of interest, do not degrade, and do not migrate from the tissue of interest due to the specific components and properties of the polymeric microspheres.

In a particular aspect, the contrast agent or imaging composition of the present invention contains highly size-uniform emulsion-polymerized polymeric microspheres that encapsulate a fluorescent dye or fluorophore that is incorporated within the microsphere. A wide variety of different polymeric microspheres are contemplated by the present invention. In one embodiment, the polymeric microspheres can be composed of biocompatible synthetic polymers or copolymers prepared from monomers such as, but not limited to, acrylic acid, methacrylic acid, ethyleneimine, crotonic acid, acrylamide, ethyl acrylate, methyl methacrylate, 2-hydroxyethyl methacrylate (HEMA), lactic acid, glycolic acid, c-caprolactone, acrolein, cyanoacrylate, bisphenol A, epichlorhydrin, hydroxyalkylacrylates, siloxane, dimethylsiloxane, ethylene oxide, ethylene glycol, hydroxyalkylmethacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethylmethacrylate, vinyl pyridine, aminoethyl methacrylates, 2-methacryloyloxy-trimethylammonium chloride, and polyvinylidene, as well polyfunctional crosslinking monomers such as N,N'-methylenebisacrylamide, ethylene glycol dimethacrylates, 2,2'-(p-phenylenedioxy)diethyl dimethacrylate, divinylbenzene, triallylamine and methylenebis-(4-phenylisocyanate), including combinations thereof. In one aspect the polymers include polyacrylic acid, polyethyleneimine, polymethacrylic acid, polymethylmethacrylate, polysiloxane, polystyrene, polydimethylsiloxane, polylactic acid, poly(ε-caprolactone), epoxy resin, poly(ethylene oxide), poly(ethylene glycol), and polyamide (nylon). In another aspect the copolymers include the following: polyvinylidene-polyacrylonitrile, polyvinylidene-polyacrylonitrile-polymethylmethacrylate, and polystyrene-polyacrylonitrile.

It should be understood that the term biocompatible as used herein to describe the polymeric microspheres of the present invention means that the polymers do not substantially interact with the tissues, fluids, and other components of the body in an adverse manner.

Examples of select microspheres known in the art include, but are not limited to, polymethylmethacrylate (PMMA) microspheres; polystyrene microspheres; polyacrylonitriles microspheres; polyacrylamide microspheres; polyvinyl chloride microspheres; poly(D,L-lactide-co-glycolide) (PLGA) microspheres; poly(epsilon-caprolactone) (PCL) microspheres; poly(D,L-lactide)/poly(D,L-lactide-co-glycolide) composite microspheres; alginate-poly-L-lysine alginate (APA) microspheres; alginate microspheres; poly(D,L-lactic-co-glycolic acid) microspheres; chitosan microspheres; poly[p-(carboxyethylformamido)-benzoic anhydride] (PCEFB) microspheres; hyaluronan-based microspheres; biodegradable microspheres; microspheres of PMMA-PCL-cholesterol; polypropylene fumarate)/poly(lactic-co-glycolic acid) blend microspheres; poly(lactide-co-glycolide acid-glucose) microspheres; polylactide co-glycolide (PLG) microspheres; poly(methacrylic acid) microspheres; poly(methylidene malonate 2.1.2)-based microspheres; ammonio methacrylate copolymer microspheres; poly(ethylene oxide)-modified poly(beta-amino ester) microspheres; methoxy poly(ethylene glycol)/poly(epsilon-caprolactone) microspheres; polyferrocenylsilane microspheres; poly(fumaric-co-sebacic acid) (P(FASA)) microspheres; polyisobutylcyanoacrylate microspheres; polyethyl-2-cyanoacrylate) microspheres; poly(DL-lactide) microspheres; poly(EGDMA/HEMA) based microspheres; glutaraldehyde crosslinked sodium alginate microspheres; pectin microspheres; crosslinked polyethyleneimine microspheres; poly(glycidyl methacrylate-co-ethylene dimethacrylate) microspheres; cellulose acetate trimellitate ethylcellulose blend microspheres; poly(ester) microspheres; polyacrolein microspheres; 2-hydroxyethyl methacrylate microspheres; or any other suitable polymeric microspheres, as well as a combination thereof.

In one particular embodiment, the present invention contemplates the use of polymethylmethacrylate (PMMA) microspheres. PMMA is a transparent and rigid plastic produced by the polymerization of methyl methacrylate and is more commonly known under the trademarks PLEXIGLAS®, LUCITE®, and PERSPEX®. PMMA is biologically inert and has been used previously for various implantable medical purposes like dental prosthesis, bone repair, orthopedics, and pacemakers. Further, PMMA has been approved by FDA for the application as dermal filler, bone cement, and a PMMA encapsulated ultraviolet dye for skin tattoos. Suitable PMMA microspheres are available from Cospheric, LLC, Phosphorex, Bangs Laboratories, Inc., and Polysciences, Inc.

Migration of implanted PMMA microspheres has been studied in an evaluation of incontinence therapy, where miniswine (laboratory swine for biomedical research applications) underwent urethral bulking with PMMA microspheres. A study of the local lymph nodes and major organs demonstrated the transport of some microspheres having a particle size of 40 micrometers or less to the local lymph nodes and lung, but not to the liver or spleen; in contrast, microspheres having a particle size of 125 micrometers were not detected in any distant organ. Thus, in order to limit the migration of the polymeric microspheres of the present invention outside of the tissue in which the polymeric microspheres are injected, the polymeric microspheres of the present invention have a particle size ranging from about 40 micrometers to about 150 micrometers, such as from about 50 micrometers to about 145 micrometers, such as from about 60 micrometers to about 140 micrometers, such as from about 70 micrometers to about 130 micrometers. In one particular embodiment and in order to further minimize migration from the direct injection site, the particle size of the polymeric microspheres can range from about 100 micrometers to about 120 micrometers. To further enhance the stability and minimize migration, the polymeric microspheres can also have a density ranging from about 1 gram/cubic centimeter to about 1.5 grams/cubic centimeter, such as from about 1.1 grams/cubic centimeter to about 1.4 grams/cubic centimeter, such as from about 1.2 grams/cubic centimeter to about 1.3 grams/cubic centimeter.

Because of the particle size and/or density of the polymeric microspheres contemplated by the present invention, the polymeric microspheres can be directly injected into tissue of interest and do not migrate therefrom. As such, the present inventor has surprisingly found that the polymeric microspheres do not require a coating to maintain stability and prohibit migration, and the polymeric microspheres of the present invention can be generally free of any coating such as a surfactant coating, a protein coating, or any other coating typically used to enhance the stability of the microspheres. Despite being generally free of any stability-enhancing coatings, the polymeric microspheres and the fluorescent dyes or fluorophores encapsulated thereby can be visible in the tissue of interest for a time period of up to about 12 months or more, such as up to about 18 months, such as up to about 24 months post-injection.

The microspheres of the present invention can be prepared by various processes as known by one of ordinary skill in the art, such as by interfacial polymerization, phase separation and coacervation, multiorifice centrifugal preparation, solvent evaporation, or a combination thereof. Suitable procedures which may be employed or modified in accordance with the present invention to prepare the polymeric microspheres contemplated by the present invention include those procedures disclosed in U.S. Pat. Nos. 4,179,546; 3,945,956; 4,108,806; 3,293,114; 3,401,475; 3,479,811; 3,488,714; 3,615,972; 4,549,892; 4,540,629; 4,421,562; 4,420,442; 4,898,734; 4,822,534; 3,732,172; 3,594,326; and 3,015,128.

Near-Infrared Fluorescent Dyes or Fluorophores

Any near-infrared fluorescent dye or fluorophore known to one of ordinary skill in the art having an excitation wavelength compatible with in vivo imaging can be encapsulated by the polymeric microspheres discussed above in order to form an imaging composition that can be directly injected into any tissue of interest. The term "fluorophore" as used herein refers to a composition that is inherently fluorescent. Fluorophores may be substituted to alter the solubility, spectral properties, or physical properties of the fluorophore. Numerous fluorophores known to one of ordinary skill in the art and contemplated for encapsulation by the polymeric microspheres discussed above include are described in more detail below. As used herein, fluorophores of the present invention are compatible with in vivo imaging, optically excited in tissue, and generally have an excitation wavelength ranging from about 650 nanometers to about 950 nanometers, such as from about 675 nanometers to about 925 nanometers, such as from about 700 nanometers to about 900 nanometers.

A fluorescent dye or fluorophore of the present invention is any chemical moiety that exhibits an excitation wavelength as described above and that is optically excited and observable in tissue. Dyes of the present invention include, without limitation, methylene blue, pyrenes, anthracenes, naphthalenes, acridines, stilbenes, indoles or benzindoles, oxazoles or benzoxazoles, thiazoles or benzothiazoles, a 4-amino-7-nitrobenz-2-oxa-1,3-diazole (NBD), cyanines or carbocyanines (including any corresponding compounds in U.S. Pat. Nos. 6,403,807; 6,348,599; 5,486,616; 5,268,486; 5,569,587; 5,569,766; 5,627,027; 6,664,047; 6,048,982 and 6,641,798), carbostyryls, porphyrins, salicylates, anthranilates, azulenes, perylenes, pyridines, quinolines, borapolyazaindacenes (including any corresponding compounds disclosed in U.S. Pat. Nos. 4,774,339; 5,187,288; 5,248,782; 5,274,113; and 5,433,896), a xanthenes (including any corresponding compounds disclosed in U.S. Pat. Nos. 6,162,931; 6,130,101; 6,229,055; 6,339,392; and 5,451,343), oxazines or benzoxazines, carbazines (including any corresponding compounds disclosed in U.S. Pat. No. 4,810,636), phenalenones, coumarins (including an corresponding compounds disclosed in U.S. Pat. Nos. 5,696,157; 5,459,276; 5,501,980; and 5,830,912), furans or benzofurans (including any corresponding compounds disclosed in U.S. Pat. Nos. 4,603,209 and 4,849,362); and benzphenalenones (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the dye is a xanthene, the dye is optionally a fluorescein, a rhodol (including any corresponding compounds disclosed in U.S. Pat. Nos. 5,227,487 and 5,442,045), a rosamine, or a rhodamine (including any corresponding compounds in U.S. Pat. Nos. 5,798,276; 5,846,737; 5,847,162; 6,017,712; 6,025,505; 6,080,852; 6,716,979; and 6,562,632). As used herein, fluorescein includes benzofluoresceins or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Fluorinated xanthene dyes have been described previously as possessing particularly useful fluorescence properties (as described in International Publication No. WO 97/39064 and U.S. Pat. No. 6,162,931).

In some embodiments of the present invention, the near-infrared fluorescent dye can include indocyanine green (ICG), methylene blue (MB), or a combination thereof.

As mentioned above, the imaging compositions of the present invention can include the aforementioned near-infrared fluorescent dye or fluorophore that is encapsulated in the aforementioned polymeric microspheres, where the composition is thus prepared from undyed polymeric microspheres. Alternatively, one or more dyes can be added to pre-dyed microspheres such as the many varieties of fluorescent microspheres available commercially, provided that the dyes have an excitation wavelength and emission spectra compatible with in vivo imaging.

The fluorescent dyes can be incorporated into the polymeric microspheres by any method known in the art, such as copolymerization of a monomer and a dye-containing comonomer or addition of a suitable dye derivative in a suitable organic solvent to an aqueous suspension of polymer microspheres. For example, the fluorescent microspheres can be produced by free radical-initiated, anaerobic copolymerization of an aqueous suspension of a mono-unsaturated monomer that may or may not contain a covalent bonding group such as a carboxyl, amino, or hydroxyl group and a fluorescent monomer mixture containing at least 10% by weight of monomers comprising the appropriate near-infrared fluorescent dye, as defined above. The fluorescent microspheres can also be produced by gradual addition of a solution of the appropriate fluorescent dyes in an appropriate solvent to a stirred aqueous suspension of microspheres, as is known in the art.

Oil-soluble fluorescent dyes, being freely soluble in organic solvents and very sparingly soluble in water, can easily be introduced by solvent-based addition of the dye to previously manufactured polymer microspheres, which can allow for the ability to prepare uniform polymer microspheres having the desired properties by following carefully optimized procedures and then later adding the fluorescent dye or dyes of choice. Furthermore, the solvent-based addition process can provided flexibility in adjusting the relative concentrations of the dyes to attain sufficiently bright fluorescent contrast agents.

In this manner, a large batch of microspheres with desired physical properties, such as particle size and density, can be prepared. Then, various fluorescent dyes can be added to smaller portions of this batch resulting in sub-batches of fluorescent dyes encapsulated by polymeric microspheres with desired spectral properties that give consistent and reproducible performance in applications. In the case of fluorescent microspheres prepared by solvent-based addition of the dye to previously manufactured polymer microspheres, the surfaces properties of the subject fluorescent microspheres are not substantially different from the surface properties of the corresponding undyed microspheres. Further, the fluorescent dye encapsulated by the polymeric microspheres is also not affected by changes in pH of the medium surrounding the polymeric microspheres.

Furthermore, the dyes used in the polymeric microspheres are not significantly removed from the polymeric microspheres by the water-based solvents that are commonly used as a suspension medium for the polymeric microspheres. In addition, the dyes are not "leaked" from the microspheres when directly injected into the tissue of interest.

In one embodiment, a single type of dye can be encapsulated by the polymeric microsphere. In another embodiment, multiple dyes can be encapsulated by the polymeric microsphere. In an additional embodiment, the dyes can include a series of dyes functioning as an acceptor and donor resulting in a longer Stokes shift than with an individual dye. In another embodiment, multiple dyes can be present that do not have spectral overlap. In this instance, the imaging composition comprises polymeric microspheres in an injectable formulation in which dyes having two emission bands, for example, one in the visible and one in the near-infrared range, would be of use. Such applications could include ex vivo post-dissection histology. The non-infrared emission of the microspheres could be used to locate the disease feature using a macroscopic imaging system. The diseased tissue with entrapped polymeric microspheres could then be more closely examined using microscopes equipped to collect and process visible light.

Regardless of the particular composition of the polymeric microspheres and near-infrared fluorescent dyes (and other dyes, if included), the dye is generally present in the polymeric microspheres in an amount ranging from about 0.01 wt. % to about 10 wt. %, such as from about 0.5 wt. % to about 7.5 wt. %, such as from about 1 wt. % to about 5 wt. % based on the wt. % of the polymeric microspheres. Further, for direct injection into the tissue of interest via a catheter or other suitable device, the imaging composition (e.g., the polymeric microsphere encapsulated fluorescent dye) can be delivered via a carrier fluid such as saline, sterile water, etc., where the imaging composition is added to the carrier fluid so that the carrier fluid has a solids content ranging from about 0.01 wt. % to about 20 wt. %, such as from about 0.05 wt. % to about 15 wt. %, such as from about 0.1 wt. % to about 10 wt. %.

System

The imaging composition described above and containing the polymeric microsphere encapsulated fluorescent dye can be used as a component of a system for visualizing a tissue of interest before, during, or after surgery or for general monitoring of the tissue. The imaging system can be used to directly inject the imaging composition into the tissue of interest. Thus, the problems of degradation and migration associated with the intravascular injection of contrast agents can be avoided. One particular embodiment of an imaging system contemplated by the present invention is illustrated in FIG. 1. Referring to FIG. 1, the imaging system 100 can be a multi-mode light source 101 that generates light for obtaining color and fluorescence images. The use of the light source 101 for obtaining different kinds of images will be described in further detail below. Light from the light source 101 can be supplied to an illumination guide 104 of an endoscope 106, which then illuminates an area of tissue 108 that is to be imaged. The system also includes a camera 107 that can be located at the insertion end of the endoscope 106. The light from the tissue 108 is directly captured by the camera 107. The endoscope 106 is similar to conventional video endoscopes, but with the added capability to provide both fluorescence/reflectance and/or fluorescence/fluorescence imaging in additional to conventional color imaging. The endoscope 106 can also incorporate a needle-tipped catheter 111 configured for insertion through the port of the endoscope 106 for direct injection of the imaging composition 109 of the present disclosure, which can be injected to the tissue in a carrier fluid 110 via a syringe 105.

Further, a controller 102 controls the camera 107 and the light source 101, and produces video signals that are displayed on a display 103. The controller 102 communicates with the camera 107 with wires or other signal carrying devices that are routed within the endoscope 106. Alternatively, communication between the controller 102 and the camera 107 can be conducted over a wireless link or any other suitable means known in the art.

The multimode light source 101 may include a laser light source that illuminates an area of interest. However, other light sources, such as LEDs, or other conventional illumination sources, such as arc lamps, halogen lamps in conjunction with a suitable bandpass filter, may be used. The area of interest may vary based on surgical requirements and the available illumination intensity and camera sensitivity.

A filter (not shown) can be placed in front of the camera lens to block excitation light from reaching the camera sensor, while allowing fluorescence light to pass through. The filter may be an near-infrared long-wave pass filter (cut filter), which may only be transparent to wavelengths greater than about 625 nanometers, or preferably a bandpass filter transmitting at peak wavelengths of between about 650 nanometers and about 950 nanometers and having a full width at half maximum (FWHM) transmission window of between about 10 nanometers and 25 nanometers (i.e., outside the excitation wavelength band). The camera 107 can also be designed to acquire a color image of the area of interest to allow real-time correlation between the fluorescence image and the color image.

It is to be understood that various known and/or commercially available imaging systems can be used in conjunction with the imaging composition of the present invention as known by one of ordinary skill in the art, including those systems by Novadaq Technologies, Inc. (i.e., the PINPOINT, SPY, FIREFLY, and LUNA Imaging Systems and those systems described in U.S. Patent Application Publication Nos. 2010/0286529 and 2013/0286176); the Firefly Robotic system; the Fluoptics Fluobeam system; Hamamatsu's Photodynamic Eye (PDE) system, and the Frangioni Laboratory's FLARE system, where such systems utilize either laser diodes or LEDs at fluence rates usually in the range of about 1 to about 10 mW/square centimeter and utilize either 12-bit dynamic range CCD cameras or 8-bit cameras. Surgical microscopes equipped with near-infrared fluorescence modules can also be used, such as the Zeiss INFRARED 800 and the Leica FL800.

Method of Tissue Marking

Figure 2:
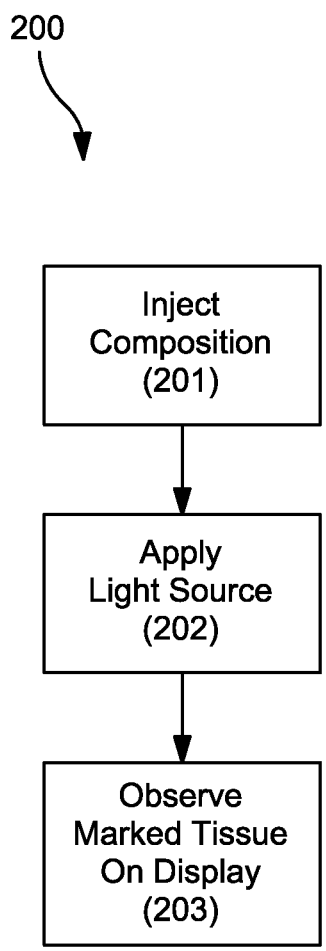
FIG. 2 illustrates a method for injecting an imaging composition into tissue for visualization according to one embodiment of the present invention.

The system described above can be used to mark tissue of interest for visualization, where one method contemplated by the present invention is illustrated in FIG. 2. Specifically, the method 200 of FIG. 2 requires steps 201, 202, and 203. Step 201 involves directly injecting a carrier fluid containing a near-infrared fluorescent dye encapsulated by polymeric microspheres into the tissue to mark the tissue, wherein the polymeric microspheres have a particle size of from about 40 micrometers to about 150 micrometers. Next, step 202 involves applying a light source to an area near the tissue, wherein the light source is applied at a wavelength sufficient to excite the near-infrared fluorescent dye. Meanwhile, step 203 involves observing the marked tissue on a display.

Systems for Tissue Dissection

Figure 3:
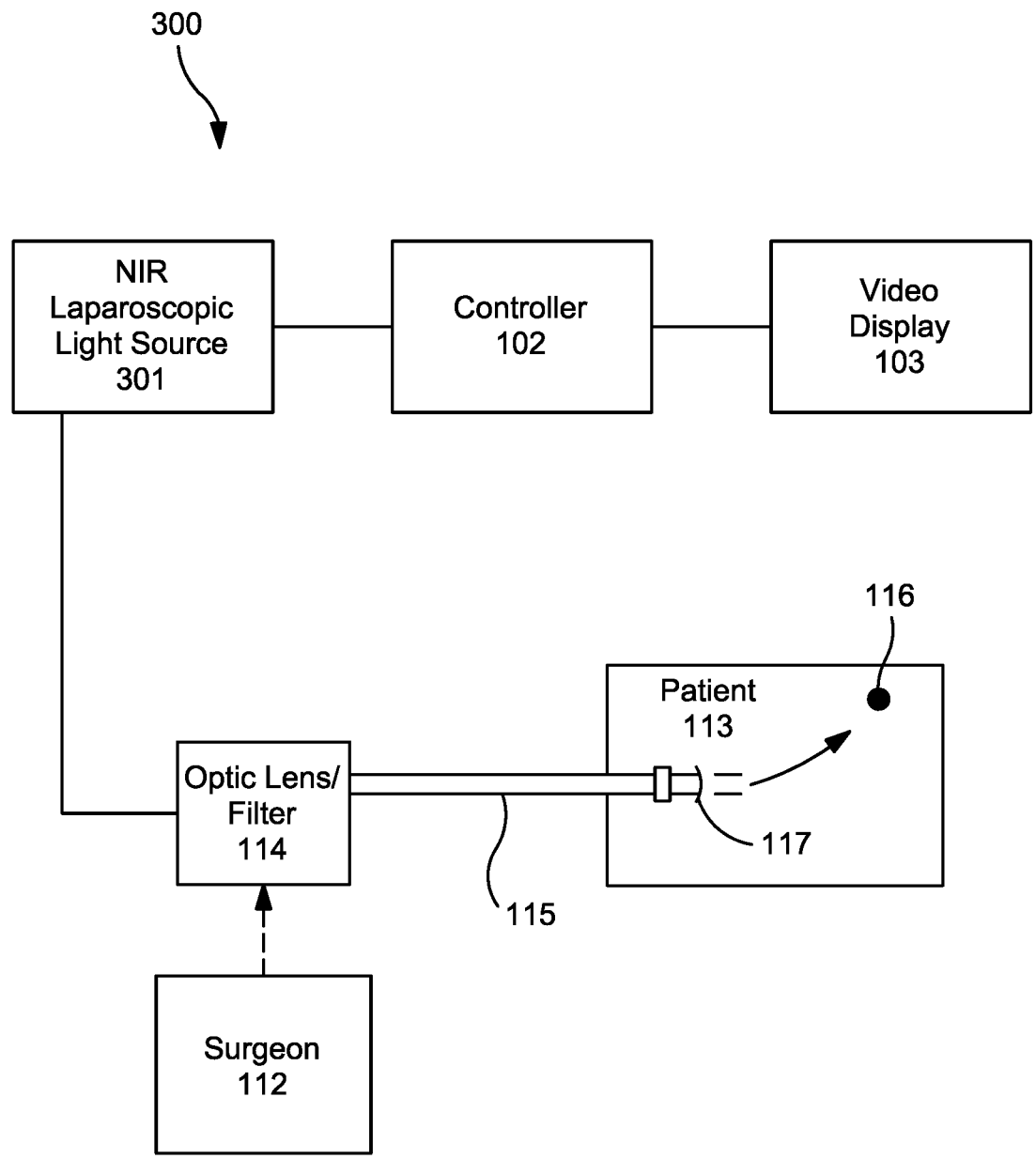
FIG. 3 illustrates a system for removing tissue marked with the composition of the present invention during a laparoscopic surgical procedure.
Figure 4:
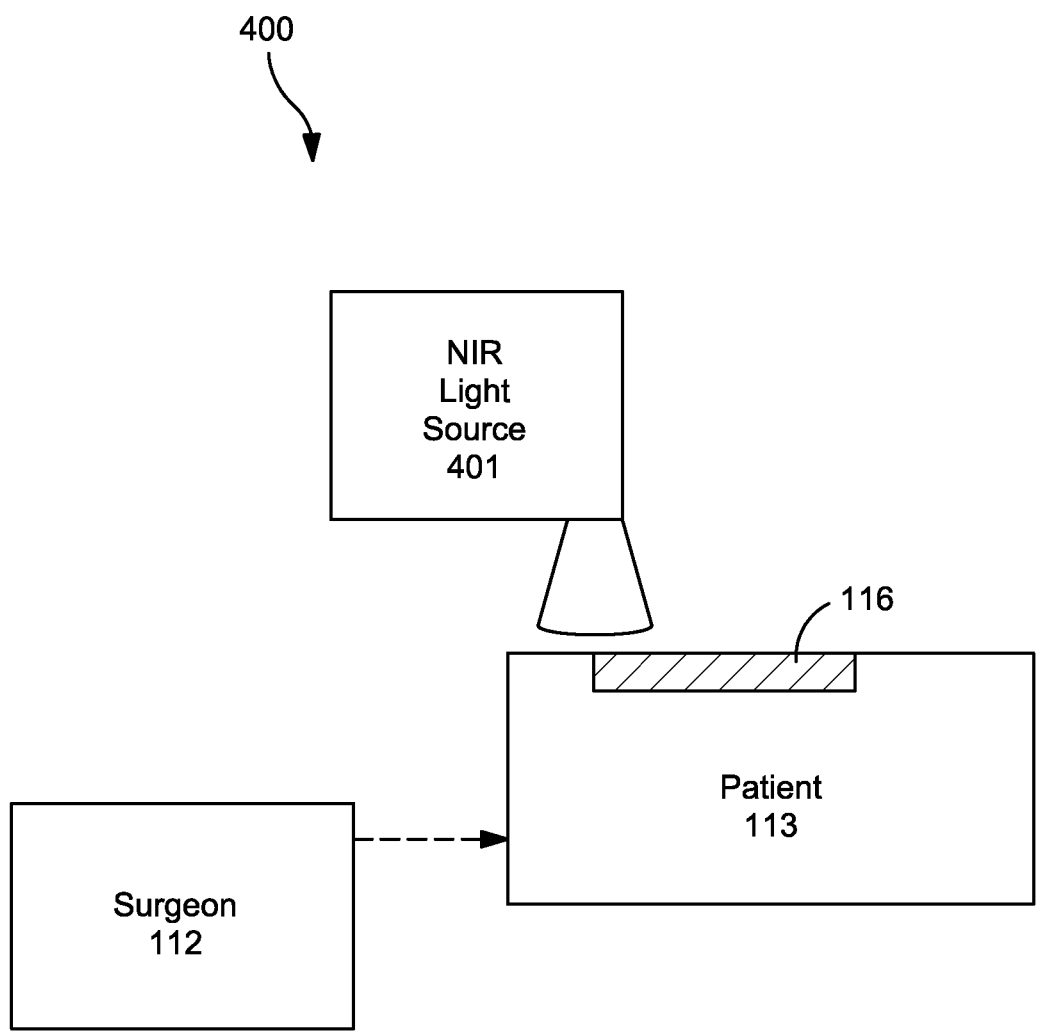
FIG. 4 illustrates a system for removing tissue marked with the composition of the present invention during an open surgical procedure.

Referring now to FIGS. 3 and 4, the present invention also contemplates a system for tissue dissection during a laparoscopic procedure and an open procedure, where both systems utilize the imaging composition 109 described above. After the tissue of interest 108 in FIG. 1 has been marked with imaging composition 109 according to the method of FIG. 2 or any other suitable direct injection method (e.g., syringe, catheter, etc.), the resulting marked tissue 116 can be easily identified and then dissected, removed, biopsied, etc. As shown, in FIG. 3, for instance, a laparoscopic imaging system 300 can include a multi-mode near-infrared laparoscopic light source 301 coupled to a video display 103 via a controller 102, where the near-infrared laparoscopic light source 301 can generate light for obtaining visual and fluorescent images. Light from the near-infrared laparoscopic light source 301 can be directed to a laparoscopic optic lens/filter 114 that can be introduced by a surgeon 112 into a patient 113 via standard techniques such as a laparoscope 115 that can be inserted at insertion site 117. The optic lens 114 can illuminate the marked tissue 116, which has been marked with the imaging composition 109 per the method described above with respect to FIG. 2. Images retrieved by the optic lens 114 are then sent to the video display 103 for visualization in real time by the surgeon 112, who can locate the tissue of concern (e.g., the marked tissue 116) for purposes of performing a surgical procedure to remove, dissect, biopsy, resect, or otherwise alter the marked tissue 116 once it has been identified via the light source 301.

Turning now to FIG. 4, an open procedure imaging system 400 is also contemplated. The open procedure imaging system 400 can include a multi-mode near-infrared light source 401 that generates light for obtaining visual and fluorescent images. The near-infrared light source 401 can be positioned directly above the patient 113 to illuminate the marked tissue 116, which has been marked with the imaging composition 109 per the method described above with respect to FIG. 2, where the marked tissue is either superficial or exposed tissue, such as, but not limited to tissue exposed during breast or open colon surgery, that the surgeon 112 will dissect once it is identified via the light source 401.

In summary, when used in conjunction with a fluorescent imaging system via either a laparoscopic or open technique, which are both commercially available, a stable near-infrared fluorescent dye encapsulated by polymeric microspheres that undergoes minimal migration and degradation post-injection could potentially improve the ease which the marked or tattooed area can be identified during surgery. In one particular embodiment, it is useful per the presently disclosed subject matter for conducting the production and utilization of encapsulating a near-infrared dye in PMMA microspheres for tissue marking for surgical excision/resection. Further, although the imaging composition is discussed herein in the context of imaging of tissue before, during, or after surgery, the present invention also contemplates any other use where imaging of an object is desired. For instance, the imaging composition can be used to monitor and track livestock or wildlife with night vision goggles. Because the imaging composition is stable with minimal degradation, livestock or wildlife injected with the imaging composition can be monitored over extended periods of time.

While the present invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for marking and visualizing tissue, the method comprising:
   injecting a carrier fluid containing a near-infrared fluorescent dye encapsulated by polymeric microspheres directly into a target tissue to mark the target tissue, wherein the polymeric microspheres have a particle size of from 60 micrometers to about 150 micrometers, further wherein the polymeric microspheres are free of a surfactant coating;
   applying a light source to an area near the tissue, wherein the light source is applied at a wavelength sufficient to excite the near-infrared fluorescent dye; and
   observing the marked tissue on a display.

2. The method of claim 1, wherein the tissue is a lesion or healthy tissue.

3. The method of claim 2, wherein the lesion is a tumor.

4. The method of claim 1, wherein the tissue is intestinal tissue, breast tissue, or brain tissue.

5. The method of claim 1, wherein the near-infrared fluorescent dye has an excitation wavelength of from about 650 nanometers to about 950 nanometers.

6. The method of claim 1, wherein the near-infrared fluorescent dye comprises methylene blue, indocyanine green, or a combination thereof.

7. The method of claim 1, wherein the polymeric microspheres comprise polymethylmethacrylate (PMMA), polystyrene, polyacrylonitrile, polyacrylamide, polyvinyl chloride, or a combination thereof.

8. The method of claim 1, wherein the polymeric microspheres have a density of from about 1 gram per cubic centimeter to about 1.5 grams per cubic centimeter.

9. The method of claim 1, wherein the polymeric microspheres are free of a surfactant or protein coating.

10. The method of claim 1, wherein the near-infrared fluorescent dye is present in the carrier fluid in an amount ranging from about 0.01 wt % to about 10 wt. % based on the wt. % of polymeric microspheres present.

11. The method of claim 1, wherein the near-infrared fluorescent dye and polymeric microspheres are contained within the tissue into which the carrier fluid is directly injected and do not migrate from the tissue.

12. The method of claim 1, wherein the near-infrared fluorescent dye encapsulated by polymeric microspheres is observed upon application of the light source for a time period of up to about 24 months post-injection.

13. The method of claim 1, wherein the light source and display are components of a fluorescent imaging system.

14. The method of claim 1, wherein the marked tissue can be dissected via a laparoscopic surgical procedure or an open surgical procedure, further wherein the carrier fluid containing the polymeric microspheres are directly injected into the target tissue through an endoscope.

15. An imaging composition for marking a tissue for visualization, the composition comprising a near-infrared fluorescent dye encapsulated by polymeric microspheres, wherein the polymeric microspheres have a particle size of from 60 micrometers to about 150 micrometers to prohibit migration of the microspheres, further wherein the polymeric microspheres are free of a surfactant coating.

16. The composition of claim 15, further comprising a carrier fluid.

17. The composition of claim 16, wherein the near-infrared fluorescent dye is present in the carrier fluid in an amount ranging from about 0.01 wt. % to about 10 wt. % based on the wt. % of polymeric microspheres present.

18. The composition of claim 16, wherein the near-infrared fluorescent dye and polymeric microspheres are contained within the tissue after direct injection into the tissue via the carrier fluid and do not migrate from the tissue.

19. The composition of claim 15, wherein the near-infrared fluorescent dye has an excitation wavelength of from about 650 nanometers to about 950 nanometers.

20. The composition of claim 15, wherein the near-infrared fluorescent dye comprises methylene blue, indocyanine green, or a combination thereof.

21. The composition of claim 15, wherein the polymeric microspheres comprise polymethylmethacrylate (PMMA), polystyrene, polyacrylonitrile, polyacrylamide, polyvinyl chloride, or a combination thereof.

22. The composition of claim 15, wherein the polymeric microspheres have a density of from about 1 gram per cubic centimeter to about 1.5 grams per cubic centimeter.

23. The composition of claim 15, wherein the polymeric microspheres are free of a protein coating.

24. A system for tissue visualization, the system comprising:
   a fluorescent imaging system comprising a light source and a display; and
   a carrier fluid containing a near-infrared fluorescent dye encapsulated by polymeric microspheres to mark the tissue, wherein the polymeric microspheres have a particle size of from 60 micrometers to about 150 micrometers to prohibit migration of the microspheres, further wherein the polymeric microspheres are free of a surfactant coating;

wherein applying the light source to an area near the tissue at a wavelength sufficient to excite the near-infrared fluorescent dye facilitates the observation of the marked tissue on the display.

\* \* \* \* \*